United States Patent

Demarest et al.

[11] Patent Number: 5,970,686
[45] Date of Patent: Oct. 26, 1999

[54] SUTURE WINDING ARRANGEMENT IN A MACHINE FOR THE AUTOMATED PACKAGING OF NEEDLES AND ATTACHED SUTURES

[75] Inventors: David D. Demarest, Parsippany; Robert A. Daniele, Flemington; Anthony Esteves, Somerville, all of N.J.

[73] Assignee: Ethicon, Inc., Somerville, N.J.

[21] Appl. No.: 09/020,191

[22] Filed: Feb. 6, 1998

[51] Int. Cl.[6] ................................................. B65B 63/04
[52] U.S. Cl. ................................................. 53/430; 53/118
[58] Field of Search .......................... 53/430, 116, 473, 53/55, 58, 118; 28/291; 242/472.7

[56] References Cited

U.S. PATENT DOCUMENTS

| 3,618,282 | 11/1971 | Hagel et al. ............................ 53/116 |
| 3,811,244 | 5/1974 | Killen et al. ............................ 53/116 |
| 3,816,889 | 6/1974 | Crotti .................................... 28/21 |
| 4,255,917 | 3/1981 | Stone .................................... 53/430 |
| 5,056,658 | 10/1991 | Sobel et al. ............................ 206/63.3 |
| 5,230,424 | 7/1993 | Alpern et al. .......................... 206/63.3 |
| 5,469,689 | 11/1995 | Demarest et al. ...................... 53/430 |
| 5,660,024 | 8/1997 | Ivanov et al. .......................... 53/430 |

*Primary Examiner*—Joseph J. Hail, III
*Assistant Examiner*—Ed Tolan

[57] ABSTRACT

A machine for the automated packaging of armed sutures or; in effect, surgical needles having sutures attached thereto and, more particularly, a suture winding arrangement in an automated machine for the high-speed individualized packaging of single or individual surgical needles each having an attached suture into a tray and detachable cover providing a suture package utilized for the packaging of the individual or single needles and attached sutures.

40 Claims, 13 Drawing Sheets

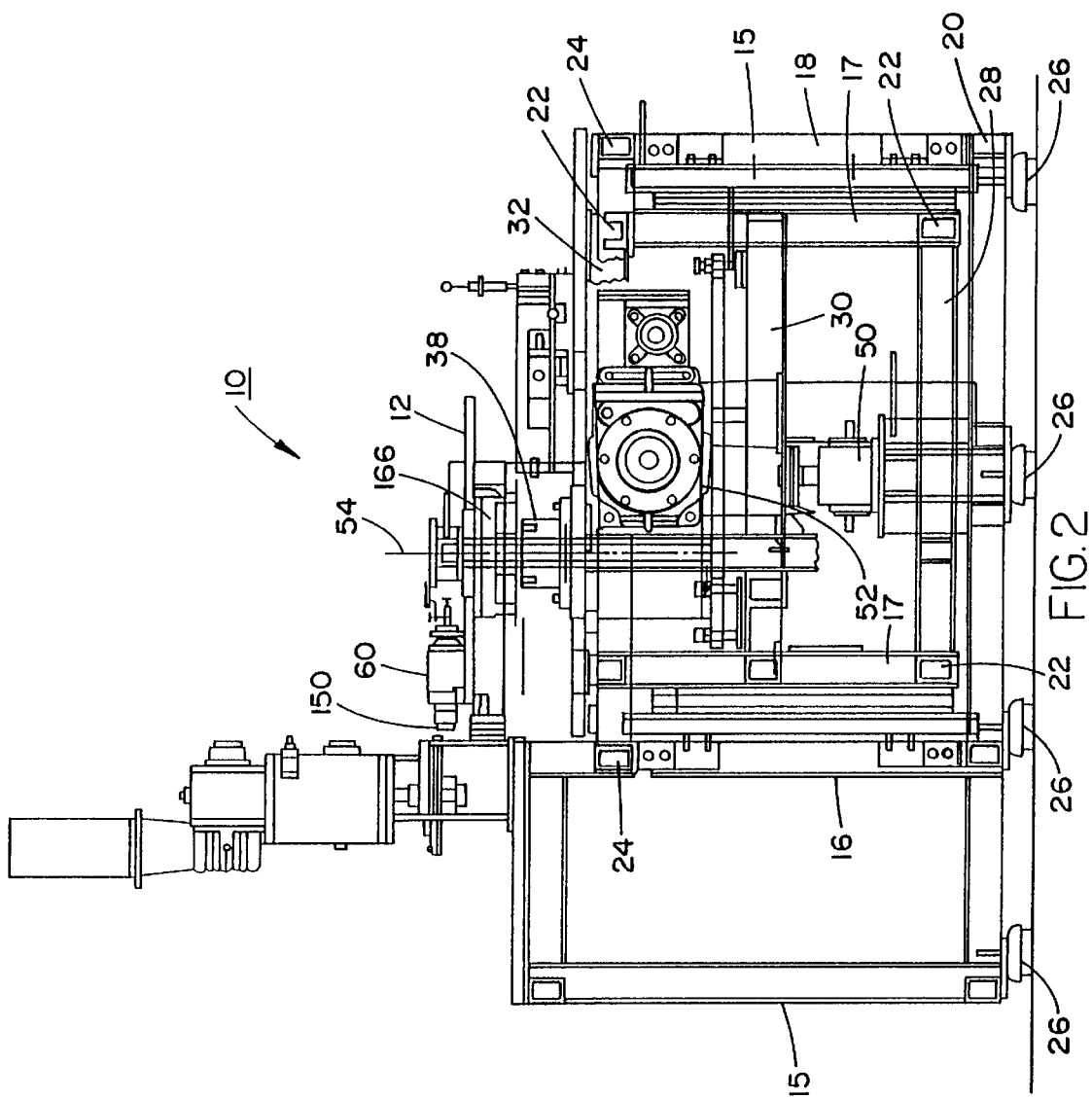

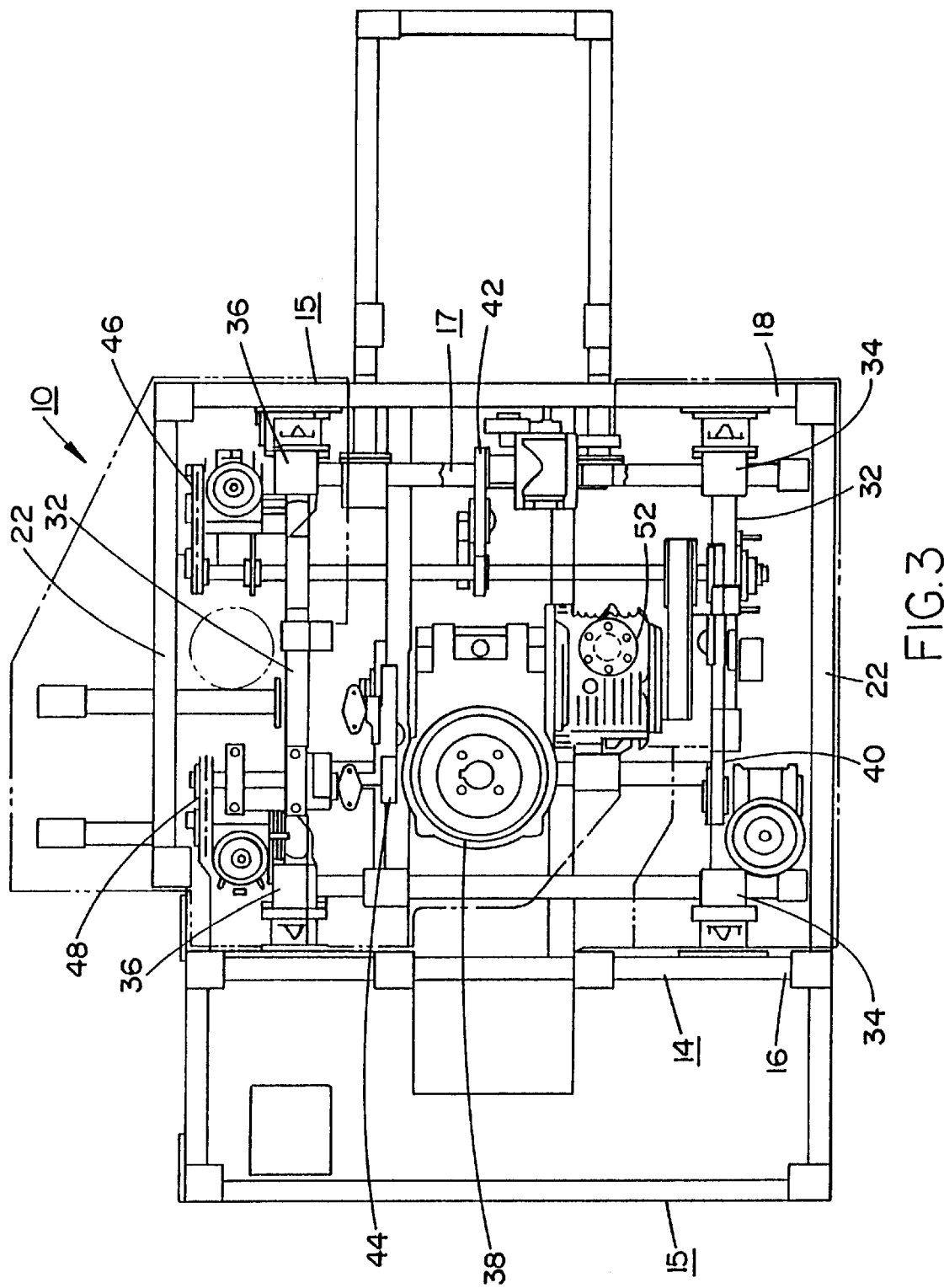

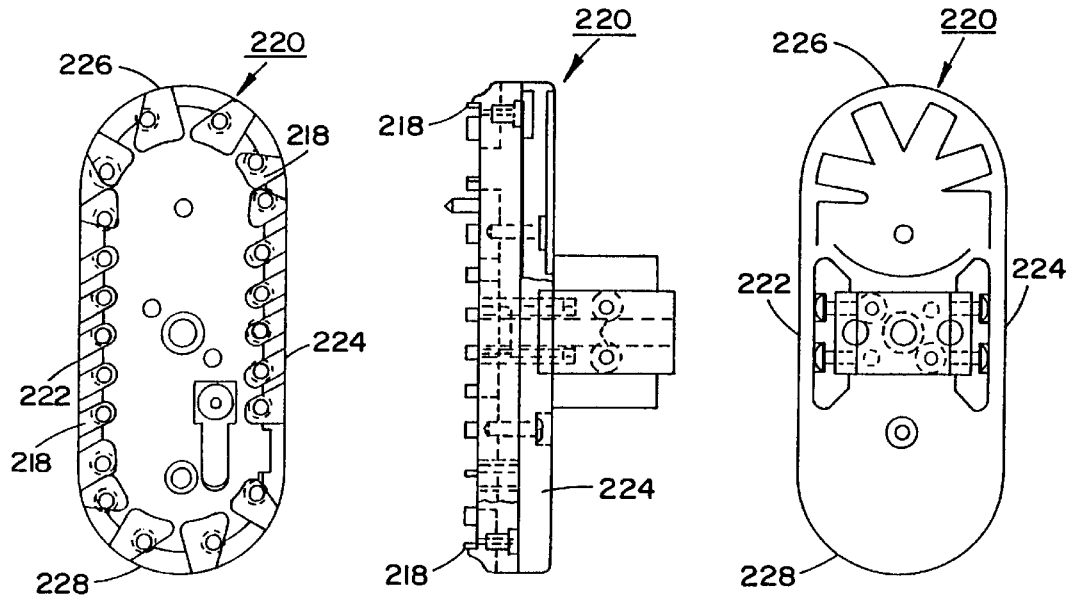
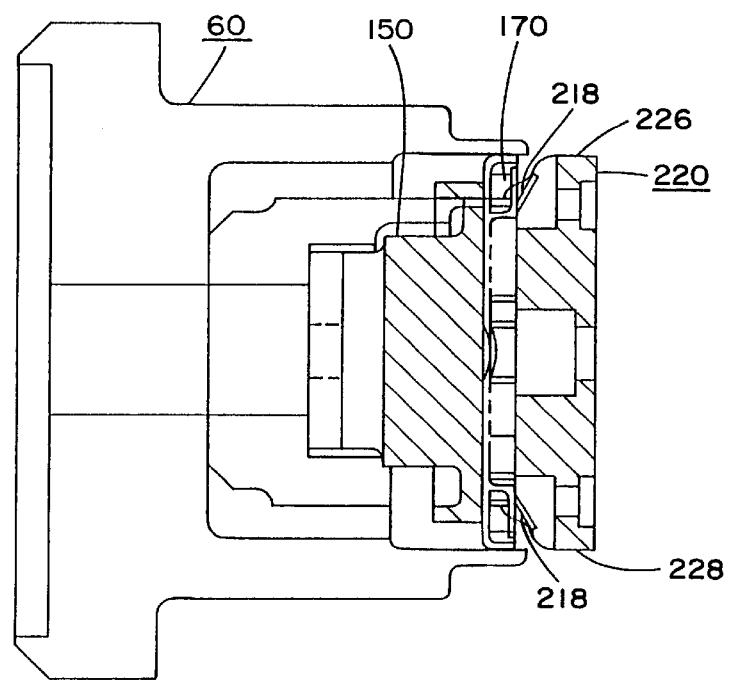

SUTURE WINDING ARRANGEMENT IN A MACHINE FOR THE AUTOMATED PACKAGING OF NEEDLES AND ATTACHED SUTURES

BACKGROUND OF THE INVENTION

1. Field of the Invention

The present invention relates to a machine for the automated packaging of armed sutures or; in effect, surgical needles having sutures attached thereto and, more particularly, pertains to a suture winding arrangement in an automated machine for the high-speed individualized packaging of single or individual surgical needles each having an attached suture into a tray and detachable cover providing a suture package utilized for the packaging of the individual or single needles and attached sutures. Additionally, the automated packaging machine incorporates operative mechanism adapted to wind the sutures into a peripheral channel of the tray and facilitating the attachment of the cover to the tray which contains the single needle and attached wound suture, and which cover concurrently constitutes a product-identifying label as a component of the tray. The cover being shaped such that removal of the cover is not necessary to enable a user to gain access to the contents of the tray; in essence, the armed suture.

The automated packaging machine also provides for a rotary turret or dial-like turntable for the high-speed loading thereof with empty trays; the sequential loading of successive forwardly indexed trays each with a needle and attached suture; the indexed advance of the needle and suture-filled tray to suture-winding stations of the machine; the conveyance of the trays each containing the needle and attached wound suture to a cover-applying station of the machine to provide the completed suture packages, and the further advance of the suture packages for subsequent automated removal of the completed suture packages from the machine. The automated packaging machine is resultingly adapted to provide for the continuous and repetitive production of suture packages in a single high-speed production cycle without necessitating any manual manipulation thereof.

In order to facilitate the production of the suture packages as described herein, the present invention provides for a plurality of sequential operating stations, in which a first station includes carousel structure having stacked package trays sequentially conveyed to a rotary plate element which slices off and separates the bottommost package tray from a stack of trays, and includes operative structure for transferring the separated package tray to a tool nest mounted on a rotary dial for transfer to subsequent processing stations, where the package tray is provided with an armed suture, the suture wound into the package tray, a cover applied thereto to produce the finished package and which is then removed from the packaging machine and further transported for additional processing and/or storage.

The present invention is specifically directed to the provision of a novel arrangement and method for the automated winding of sutures employed in the packaging of individual surgical needles and attached sutures into the package trays, so as to thereafter enable the application of covers thereto in sequential production steps through the intermediary of the automated packaging machine.

In order to effectuate the winding of the sutures into the package trays there are provided two successive winding workstations wherein, at a first winding workstation, the package tray is rotated so as to be oriented in an essentially horizontal direction and thereafter, at a second workstation, rapid winding is effected so as to enable a winding head to insert the sutures into peripheral channel structure formed in the package trays.

Currently, in the medical, surgical and health-related technology, the high-speed and efficient packaging of either single or multiple sutures which are each suitably attached to surgical needles, such as by being swaged or similarly fastened thereto, and in which such combined sets of needles and sutures are generally referred to as armed sutures, is imparted an increasing degree of importance in view of the rising demand of users for such combined surgical needles and attached sutures, and various diverse types of inexpensively manufactured suture packages for the containment of needles and attached sutures have been developed and are presently widely employed.

In specific instances, suture packages may be covered tray-shaped containers designed to receive and fixedly retain therein one or more needles and therewith attached sutures, in which the suture packages, upon opening of the covers, must enable the uncomplicated and simple withdrawal of a respective individual needle and its attached suture in a smooth unobstructed manner. In essence, when the needle which is to be removed from the suture package is engaged by a surgeon or health professional, for example, by being gripped through the intermediary of a forceps and then pulled out of the suture tray, it is essential that the needle easily disengage from its restraint in the package while the suture which is attached to the needle should also be readily able to slip out of the tray in the absence of any binding or snagging, and in the instance of the tray housing a plurality of armed sutures also without becoming entangled with other sutures still remaining in the suture tray or package. Thus, pursuant to a specific needle and suture package construction which, for example, may comprise an injection-molded plastic tray, the needles are generally engaged by clamping structure located in the tray so as to be "parked" or retained in predetermined position or array in a central region of the tray. The sutures extending from the needles to which they are attached, while being captured and maintained in a state of controlled tension are then conducted into and wound so as to be deposited in a peripheral channel formed within the suture tray while the latter is rotated so as to extend along the peripheral length of the channel.

This positioning of the needles, and particularly that of the sutures within the peripheral channel of the tray is intended to eliminate tight bends or curves normally imposed on the sutures so as to facilitate their easy withdrawal from the suture package.

2. Discussion of the Prior Art

Until relatively recently, the introduction of needles with attached sutures into suture packages or molded plastic trays was being implemented in a substantially manual manner. In that instance, the needles were manually, placed into the tray so as to be clampingly engaged by means of suitable needle-gripping structure, and thereafter the attached sutures wound or positioned within the confines of the tray. Subsequently, a suitable cover was superimposed upon and fastened to the filled tray, and the resultant armed suture package conveyed to a suitable arrangement for possible sterilizing or further over wrapping.

The foregoing essentially manual and relatively basic process for winding the sutures into the tray, and especially the locating thereof into the peripheral channel of the tray during manipulation of the tray, was quite time-consuming, and in conjunction with the manual application of the cover into the tray in a basically individual or piece-by-piece mode, represented a serious hindrance to a large volume or mass produced manufacturing output, and adversely affected the economics in attempting to provide such large quantities of suture packages containing either single or multiple surgical needles and attached sutures.

As an improvement over the foregoing, there was then developed a generally semi-automated winder machine for packaging surgical needles and attached sutures in a tray-like suture package, and wherein at least some of the previously manually implemented packaging steps were to some extent automated in order to be able to increase the output of needle and suture-containing packages while simultaneously reducing the number of manual procedures in effectuating the packaging of those particular items.

To that effect, the semi-automated winder machine, although necessitating the manual orientation of the trays for implementing the filling thereof with needles and attached sutures, included a winding station which to a considerable degree automated the winding process for the sutures so as to place the latter into a peripheral channel extending about the circumference of the tray. Also provided was a further therewith operatively associated device which enabled covers to be manually placed on the needle and suture-filled trays to be fastened thereto by means of a pressing die forming latchingly engaging interconnections between each of the covers and the trays, while concurrently producing from a portion of the cover a product-identifying label which remains permanently attached to the tray upon subsequent detachment of the cover. Although providing a considerable advance over the state-of-the-art in the packaging of needles and sutures, the semi-automated winder machine nevertheless necessitated the implementation of a considerable number of manual and labor-intensive handling steps in effectuating the filling of the trays with surgical needles and attached sutures, attaching the cover and, generally, producing complete suture packages.

As a further technological advance over the foregoing semi-automated needle and suture packageforming concept, there was then developed a substantially fully automated packaging machine which is adapted, in a highly efficient and extremely rapid mode, to continually fill successive trays of the type described hereinabove with pluralities of surgical needles and attached sutures, and subsequently causing the sutures to be wound into the confines of the tray, such as into a peripheral channel extending about the tray. Thereafter, the packaging machine was designed to implement the automated positioning and fastening of covers to the needle and suture-filled trays to produce completed suture packages of the type described hereinabove, which were then adapted to be transported to a suitable locale for selective further processing, such as sterilizing, and/or over wrapping, as is required by this technology.

In particular, the automated packaging machine was designed to provide the packages with each housing a plurality of needles and attached sutures. For example, the packaging machine for accomplishing the foregoing, which is commonly assigned to the assignee of the present application, is described in U.S. Pat. Nos. 5,487,212; 5,473, 854; 5,469,689; 5,473,810; 5,511,670; 5,452,636; 5,438, 746; 5,500,991; 5,477,609; 5,485,668; and 5,487,216.

The flat, tray-shaped suture package produced by the packaging machine set forth in the above-mentioned patents provides for the storage therein of multiple surgical needles and attached sutures, while concurrently recognizing the need to facilitate the smooth and unobstructed withdrawal of individual needles and attached sutures from the suture package. For instance, such a suture package is disclosed in applicants, U.S. Pat. No. 5,230,424, which is commonly assigned to the assignee of the present application; and wherein the suture package is referred to as an RSO package (Reduced Size Organizer).

In the specific design of the flat trayshaped plastic container having a peripheral channel as disclosed in the above-mentioned patent, the suture package is basically constituted of a rectangular round-cornered and flat-bottomed injection-molded plastic tray having a flat central surface area including a raised needle clamping structure formed thereon for engaging and "parking" a plurality of needles in a predetermined spaced array. Sutures each have one end thereof attached to each of the respective needles so as to form so-called "armed sutures". The sutures extend from each of the needles into a channel extending about the perimeter or periphery of the suture tray and are conducted into the channel so as to be essentially wound within the circumferential confines of the suture tray. The plurality of sutures which are positioned within the suture tray channel are protected against inadvertent outward displacement therefrom through the presence of a multiplicity of contiguously positioned resilient fingers which are integrally molded with the suture tray, and which project outwardly above the confines of the channel along a major portion of the length of the channel and, collectively, form a so-called "zipper structure" in which the inherently resilient nature of the fingers facilitates their temporary raising up to enable the introduction of the sutures into the suture tray channel by means of a suitable suture winding apparatus.

Although the rotary dial or turntable apparatus of the packaging machine pursuant to the foregoing U.S. patents provides for the packaging of armed sutures; in effect, needles with attached sutures, in a rapid and fully automated manner, such as by supplying the tray-shaped packages; thereafter parking the plurality of armed sutures in the packages, applying covers and removing the completed suture packages from the machine in a sequential station-to-station procedure, the machine was designed to primarily produce suture packages each containing a plurality of armed sutures.

SUMMARY OF THE INVENTION

Pursuant to the present inventive concept, the above-mentioned automated packaging machine is further improved upon in a novel and unique manner in that the machine is adapted to produce suture packages each containing a single armed suture, such packages being frequently in demand rather than packages containing a plurality of needles and sutures. Thus, in order to provide for high production rates which are essentially compatible with those employed in the manufacture of suture packages each containing a plurality of armed sutures, the present invention contemplates the provision of a fully automated packaging machine with a considerably increased rate of operating speed and production capability so as to render the packaging machines economically viable in comparison with the previously described automated packaging machine, while maintaining structural and functional reliability and ease of construction and maintenance.

In order to attain the essentially automated packaging of singly-packaged or individual surgical needles with attached sutures, the automated packaging machine pursuant to the invention sets forth the provision of a rotary turret or dial-like turntable having a plurality of tool nests each possessing a suture tray supporting surface, with each tool next being circumferentially spaced about the turntable so as to be uniformly distributed about the periphery thereof. The rotary turret is rotated to cause the tool nests supporting packaging trays to be indexed forwardly so as to advance through a plurality of successive workstations which are adapted to, respectively, effectuate the supplying of each of the trays located on the tool nests or support surfaces with a single or individual surgical needle and attached suture, winding the suture into the confines of each needle and suture-containing tray, forming a latching engagement between a tray cover and the tray; and thereafter conveying each completed suture package to a station for removal from the machine and transfer to stacking bins or the like.

Operatively communicating in synchronism with the indexing rotation of the rotary turret is a carousel device housing stacks of trays, which is adapted to supply empty trays sliced or separated from the bottom of a respective stack of the trays to a rotatable platform, and includes operative robotic pivot arm structure to successively remove the trays from the rotatable platform and mount the empty trays on successive tool nests so as to be oriented in a vertical plane facing radially outwardly of the rotary turret. Thereafter, each tray is indexed sequentially forwardly by the rotary turret to a workstation at which there is imparted movement to the portion of the tool nest having the tray supported thereon, whereby the tray remains oriented essentially vertically as it is rotated angularly relative to the horizontal plane of rotation of the rotary turret. This movement enables a transfer device with a needle and suture swaging mechanism processing needle grippers at a further workstation to insert and position a surgical needle with its attached suture into a therewith aligned tray for retentive engagement with needle-engaging structure formed in the tray so as to grip and park the needle therein, with the suture extending from the needle and depending downwardly therefrom outwardly of the tray. The needle and suture-containing tray is then advanced forwardly on its respective tool nest to successive workstations responsive to indexed rotation of the rotary turret wherein, at a first suture winding station, structure operatively cooperating with the tray and the tool nest supporting the tray imparts an initial rotational movement to the tray about an axis perpendicular to the plane of the while maintaining the depending suture under tension, and at a second subsequent winding station imparts a rapid winding motion to the tray over multiple predetermined rotations so as to fully wind the downwardly depending suture into a peripheral tray channel extending within the perimeter of the tray.

At the second winding workstation, there is provided a winding head which incorporates operative structure engageable with resilient fingers of the packaging tray which extend over the peripheral channel formed in the tray. This, during the winding or rotating motion of the winding head causes the resilient fingers to be successively raised to thereby wind the suture into the tray channel.

Thereafter, the tool nest mounting the tray with the needle parked therein and the attached suture which has been wound into the peripheral channel of the tray is advanced to a further workstation responsive to indexed rotation of the rotary turret; at which workstation an operating mechanism causes a bottommost cover to be sliced or separated from a stack of covers and transferred to a rotatable platform. The cover is then engaged by a robotically-controlled pivot arm which, under the action of a vacuum, pivots the cover into a vertical orientation and applies the cover onto the tray while concurrently imparting pressure to the cover to cause cooperating latching structure to clampingly fasten the cover to the needle and suture-containing tray. Upon completion of the cover-attaching sequence, the resulting completed suture package is indexed to a further workstation at which, suitable gripper arm mechanism engages the suture package, and the suture package is disengaged from the tool nest on which it is supported and conveyed, transferred to and stacked in a repository or receiving unit to be readied for further processing, such as sterilizing, overwrapping or the like, as may be required.

The foregoing sequence of operative steps is continually repeated for each successive tool nest on the rotary turret or turntable sequentially receiving empty trays from the carousel, while preceding tool nests each mounting a tray are conveyed through the above-mentioned packaging cycle. Thus, a successive tray is always placed into a position of readiness at a following or subsequent workstation and processed in a similar manner as before described during the forward indexing motion of the rotary turret or turntable. This ensures a continuously repetitive packaging cycle for successive suture packages in a highly efficient and high-speed operation without the need for any manual intervention in the operation of the packaging machine.

Intermediate various of the workstations as set forth hereinbefore; there may be arranged other workstations incorporating sensors adapted to enable the ascertaining of the presence of empty trays at the initial workstation, for a verification of a needle having been inserted into the trays and for inspection of the trays subsequent to the winding of the sutures into the tray channels; checking for the application of the covers to the trays, and facilitating the possible ejection of incomplete trays or removal from the machine of defective packages.

Pursuant to the invention, there are provided successive winding mechanisms at workstation locations subsequent to the workstation along the path of rotation of the turntable at which the surgical needle and an attached suture have been transferred into the package tray, as shown along the direction of rotation of turntable 12 defined by arrow A in FIG. 1. While a portion of the suture which extends downwardly out of the tray is captured by a clamping arrangement and also a plurality of vacuum nozzles employed for tensioning the suture, at a first winding workstation the package tray is rotated through an angle of 163.5° so as to compensate for the initial 16.5° tilt, while inverting the tray about the longitudinal axis thereof. Thereafter, the tray is advanced to a further winding workstation, where a second winding head mechanism will rapidly impart rotation to the package tray and incorporates tray-engaging structure to insert the suture portion extending outwardly of the tray into a peripheral channel located in the tray.

Accordingly, it is an object of the present invention to provide novel winding mechanism for winding a suture portion which extends outwardly from the tray into the package tray in a rapid and controlled manner.

Another object of the present invention is to provide for a two-step suture winding sequence, in which an initial winding step at a first workstation orients the package tray inverted so as to extend along the longitudinal axis thereof, and a second workstation includes winding head mechanism for imparting rapid rotation to the tray and to engage the tray so as to wind the entire length of the suture into a peripheral channel within the tray through the intermediary of suitable tray-engaging structure.

Yet another object of the present invention resides in the provision of suture winding workstations as described herein whereby winding head structure of a rapid winding mechanism engages resilient finger structure extending over a peripheral channel formed in the packaging tray so as to facilitate the winding insertion of the sutures into the peripheral tray channel.

Still another object of the present invention is to provide a method for winding the suture portion depending from the package tray into the confines of a peripheral channel formed in the tray.

A further object of the present invention is to provide a two-stage method for winding a suture into a packaging tray mounting a surgical needle and to which one end of the suture is attached with portions of the suture initially depending outwardly of the packaging tray.

A still further object of the present invention is to provide a two-stage suture winding method wherein the suture, during the second winding stage, is rapidly wound into a peripheral channel formed in the packaging tray.

BRIEF DESCRIPTION OF THE DRAWINGS

Reference may now be had to the following detailed description of a preferred embodiment of the invention, taken in conjunction with the accompanying drawings; in which:

FIG. 2 illustrates a side elevational view of the machine frame of FIG. 1;

FIG. 3 illustrates a top plan view of the machine frame of FIG. 2;

FIG. 16, 17 and 18 illustrate, respectively front, side and rear views of a winding head for winding the sutures into the trays; and FIG. 19 illustrates a sectional view of the winding head in operative engagement with a packaging tray for winding sutures into the tray.

DETAILED DESCRIPTION OF THE PREFERRED EMBODIMENT

Figure 1:
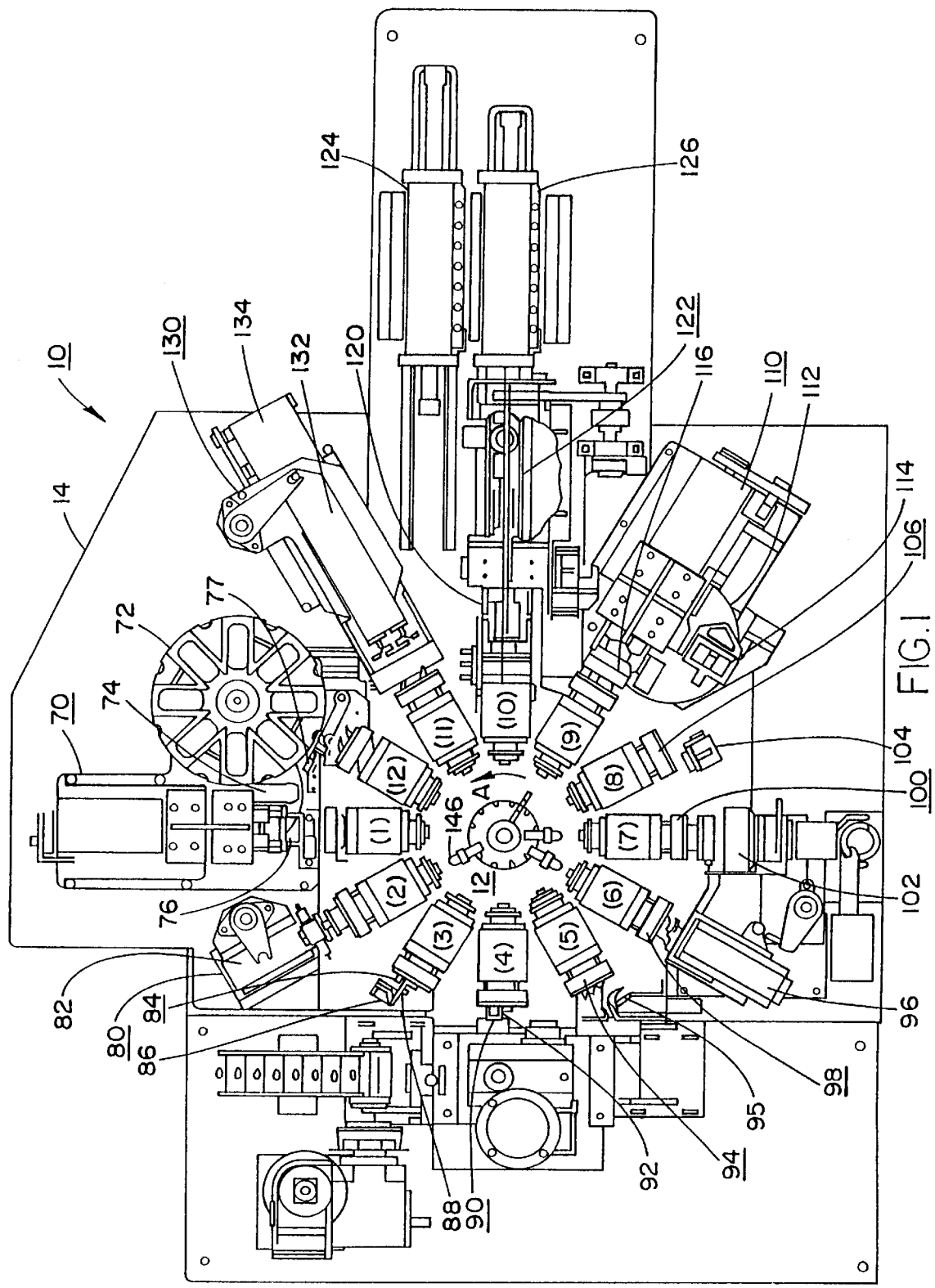
FIG. 1 illustrates generally diagrammatically, a plan view of the machine for the automated packaging of individual surgical needles and attached sutures, pursuant to the present invention.

Referring now in more specific detail to the drawings, FIGS. 1 to 3 illustrate, in a generally diagrammatic plan view, the automated needle and suture packaging machine 10 pursuant to the invention. The machine 10 comprises a rotary turret or turntable 12 which is essentially a packaging dial supported on an essentially stationary machine frame structure 14.

Figure 4:
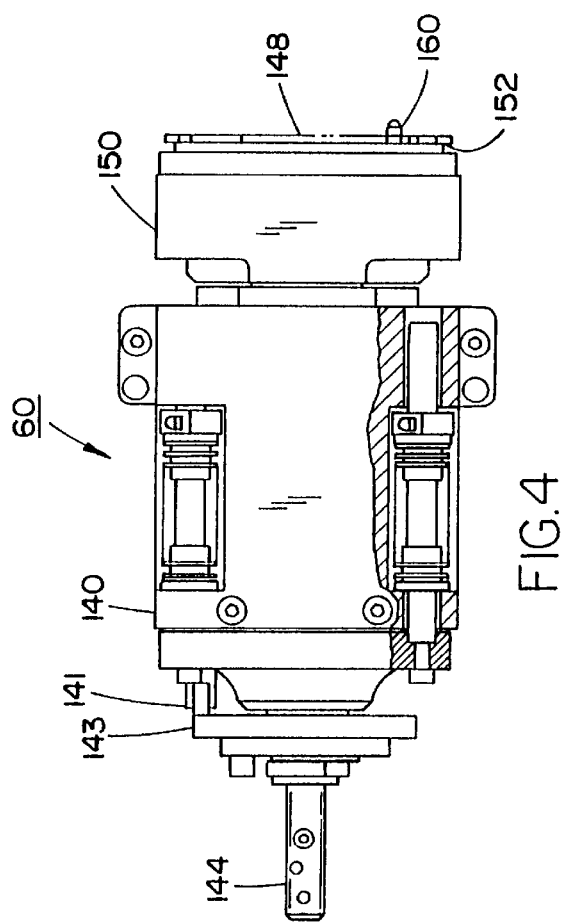

The rigid frame structure 14, as illustrated in FIGS. 2 through 4, basically includes structural uprights 16 and 18, which are interconnected by horizontal beams 20, 22, 24, with the entire frame structure 14 adapted to be supported on a floor through the intermediary of adjustable leveling footings 26. The frame structure 14 comprises an outer stationary frame arrangement 15, and an inner vertically adjustable frame arrangement 17 comprising horizontal beams 28, 30 and 32, and vertical beams 34, 36 interconnected therewith supporting the turntable 12 for vertical adjustment relative to the stationary machine frame components. The vertical adjustment of the frame arrangement 17 is provided for by a central servo motor actuated jack-screw 38, which also concurrently effectuates the vertical adjustment of all of the operative packaging devices at the various workstations of the machine so as to accommodate the packaging of a wide range of differently sized surgical needles without the necessity for modifying any machine components. Arranged within the frame structure are the various belt drives 40, 42, 44, 46 and 48 and operating drive components 50 for the machine, and the vacuum-generating systems 52 employed in the packaging cycles for the suture packages, as described hereinbelow. The turntable 12 is oriented in a horizontal plane, and through the intermediary of a program-controlled drive installation, is rotatable in an indexing or incrementally angular advance about a central vertical axis 54. In this instance, during operation of the machine, the turntable 12 is rotated in a counter-clockwise direction when viewed from above, as represented by arrow A, so as to be advanced in 30° increments.

The rotary turret or turntable 12 is essentially constituted of a circular disk-shaped member or packaging dial which has a plurality of tool nests 60 mounted thereon. The tool nests 60 are mounted in a circumferentially uniformly spaced array on the upper surface of the package dial or rotary turret 12, and with each tool nest 60 having an outer end projecting radially outwardly of the peripheral edge of the turret or dial 12, as described hereinbelow.

In this particular construction of the packaging machine 10, by way of example, twelve (12) tool nests 60 are arranged at uniformly distributed annular spacings of 30° from each other about the circumference of the dial or rotary turret 12.

In essence, as mentioned hereinbelow, the rotary turret or turntable 12 of the packaging machine 10 is adapted to be indexed forwardly in an angularly incremental or indexed rotational advance, each such incremental advance comprising one-twelfth of the 360° circumferential rotation of the turntable, or basically 30°, along the direction of rotation identified by arrow A in FIG. 1, such that the tool nests 60 which are each adapted to mount a suture tray or package are designed to be advanced in sequence to a number of successive workstations; designated herein as workstations (1) through (12), which are stationarily evenly spaced about the periphery of the rotary turret 12, as illustrated in FIG. 1 of the drawings.

The successive workstations which collectively constitute the automated machine 10 for the packaging of surgical needles and attached sutures are essentially briefly described as follows; viewed in the direction of rotation of arrow A:

(1) A first workstation 70 relates to the operative aspect of empty suture package trays being successively separated from the bottom of stacks of trays contained in a rotary carousel 72 to be transferred onto a rotationally indexed plate 74 under the action of a vacuum, and thereafter picked up and transferred by a cam-controlled robotic pivot arm structure 76 to successive tool nests 60 so as to be retained thereon while being conveyed by the rotary turret or dial 12 to subsequent workstations, as set forth hereinbelow.

(2) At this workstation 80, to which the respective tool nest 60 supporting the empty tray thereon has been advanced by the rotational advance of the turntable 12 mounting the tool nest; in effect, indexed 30° forwardly; operative slide-controlled pivot structure 82 engages a plate element on the outer end of the tool nest 60 which supports the empty tray under a vacuum, and rotates the plate element and tray counterclockwise within the vertical plane thereof about a horizontal radial axis of the tool nest 60 through an angle of approximately sixteen and one-half (16.5°) degrees so as to be in appropriate angular orientation relative to a horizontal axis for facilitating the subsequent insertion and retention of a surgical needle and attached suture into the tray.

(3) This workstation 84 provides for a sensor 86 which is mounted stationarily on a bracket arrangement 88 and faces the tool nest 60 so as to be able to check for the presence of an empty tray on the tool nest. The sensor 86 is suitably aimed at a black spot present on the packaging tooling nest, and in the absence of a tray being positioned thereon, enables deactivating the forward advance of the turntable 12 and concurrently may emit a signal to alert personnel regarding the missing tray.

(4) The next workstation 90 along the rotational path of motion of the turntable in the direction of arrow A, provides gripper mechanism 92 for inserting a single surgical needle and a therewith attached suture into the suture tray which has been indexed forwardly by the rotary turret 12 so as to be located in operative alignment with the needle-feed mechanism. The needles are conveyed by a mechanism so as to be mounted on suitable clamping or needle "park" structure constituting an integral portion of the tray. Vacuum-controlled suture capture and tensioning devices which are located below each tool nest 60, become operative at this workstation to capture and tension the suture portions depending outwardly and downwardly of the tray mounting the surgical needle.

(5) At this workstation 94, a stationary sensor 95 located radially outwardly of the turntable 12 may be utilized to ascertain the presence of a surgical needle and attached suture having been properly introduced into the tray at the previous workstation 90.

(6) A first tray winding mechanism 96 at this workstation 98 engages the plate element on the tool nest supporting the tray, while the suture capture and tensioning device ensures that the suture portion depending outwardly and downwardly from the tray is maintained under tension by a vacuum-operated tensioning device associated therewith, with the tray being rotated counterclockwise within its vertical plane through approximately 163.5°, to assume a horizontal orientation which is 180° inverse to its original orientation on the tool nest 60 at workstation (1), and with the remaining length of the suture being tensioned by the vacuum device externally of the tray.

(7) At a subsequent workstation 100, a further winding mechanism 102 engages the tool nest 60 and the tray mounted thereon, and imparts rapid rotation to the tray so as to enable tray structure engaging portions of the mechanism to introduce and completely wind the entire remaining length of the suture into a peripheral groove extending about the confines of the tray.

(8) A stationary sensor 104 at this workstation 106 is located radially outwardly of the turntable 12, and is adapted to ascertain the positioning of the surgical needle in the tray.

(9) This workstation 110 provides apparatus for the application and attachment of a cover or label to the tray containing the surgical needle and attached suture to produce or complete suture to produce a complete suture package. A rotatably indexed disc-like plate 112 includes a plurality of equidistantly circumferentially spaced cover-receiving areas, these being rotated below a vertical stack 114 of covers or labels such that, under the action of a vacuum, the bottommost covers of the stack are sequentially sliced off or separated and deposited into a respective area of the plate under the influence of the vacuum present therebeneath, and thereafter rotated into radial alignment with a tool nest 60 mounting the tray containing the surgical needle and attached wound suture. A cam-controlled robotic pivot arm structure 116 lifts the cover from the plate, while a subsequent area receives a further cover from the stack for transfer onto a following tray, and pivots upwardly and extends horizontally forwardly so as to position the cover into latching engagement with the tray, thereby forming the completed suture package.

(10) A robotic pivotable gripper arm 120 removes the completed package from the tool nest 60 at this subsequent workstation 122, and swings downwardly so as to deposit the completed suture package into receiving bins or compartments within elongated tray members 124 whereby upon a certain amount of trays being deposited to fill the tray member the latter is indexed to align a further empty compartment of a tray member with the tool nests. The tray member having the various filled compartments is then conveyed to a storage unit 126 and replaced automatically by another empty tray member.

(11) In the event of a suture package being defective, such as having a cover lacking or misplaced, and the resultant package has accordingly not been removed at the preceding package unloading workstation 122; at this workstation 130 a reciprocating arm structure 132 has a gripper head which engages and removes the rejected packages from the tool nests, and deposits them onto a conveyor belt 134 for conveyance to a suitable waste disposal site.

(12) A sensor 77 at the final workstation on the packaging machine 10 checks for the presence of a package that may not have been removed at stations (10) and (11). This is a further safegard built into the packaging machine to ensure that the tool nest at station (1) is empty and ready to accept an empty package tray.

Figure 6:
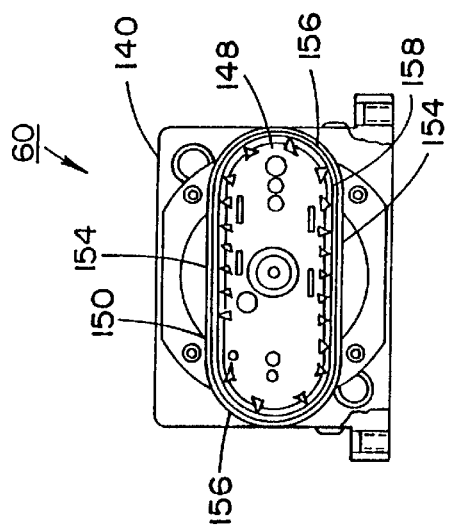
FIGS. 4, 5 and 6 illustrate, respectively, side, top plan end front end views of a tool nest utilized in the machine of FIG. 1.
Figure 5:
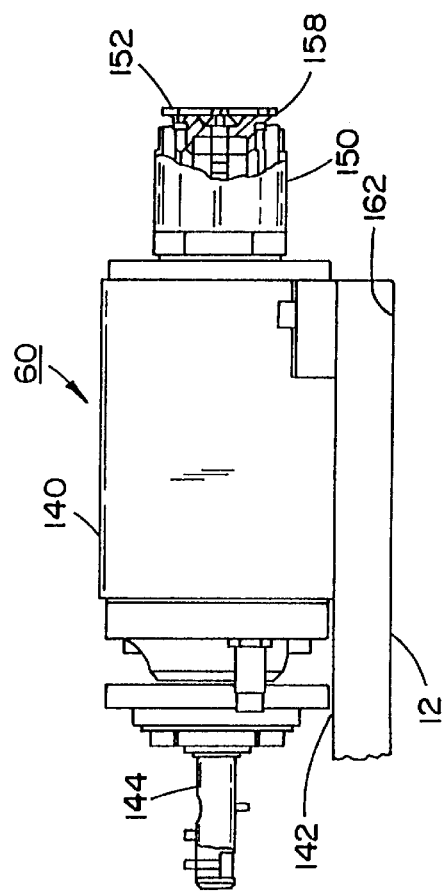

As shown in FIGS. 4 through 6, each tool nest 60 includes a housing 140 which is fixedly mounted on the upper surface 142 of the rotary turret 12. Each housing 140 includes a horizontal radially extending central through bore having a shaft 144 rotatably journaled therein. The shaft 144 is normally secured against rotation within housing 140;

however, at predetermined workstations of the machine, the shaft 144 may be released by means of a locking pin 141 so as to be axially radially inwardly movable within housing 140 against stationary cam structure 143 mounted centrally on the rotary turret or dial 12 for regulating the rotational displacement which may be imparted to the shaft 144, as discussed hereinbelow in more specific detail.

The radially outwardly facing structure 148 of a plate element 150, which is fixedly secured to the radially outer end of shaft 144, is adapted for supporting suture package components, and particularly the package trays which are utilized in the production of surgical needle and attached suture-containing packages.

In essence, the radially outer structure of the tool nest housing 140 for mounting suture trays includes the plate element 150 which comprises an elongate vertically oriented plate member 152 having generally parallel opposite sides 154 and convexly rounded opposite ends 156 so as to be generally in conformance with the peripheral shape of a package tray. An external planar surface on the plate member 152 includes protruding perimeter or rim structure 158 for seating engagement therein of a suture tray, with the plate member 152 being fixedly secured to the radially outer end of the shaft 144 so as to be adapted for rotation therewith. Extending forwardly from the external planar surface of the rotatable plate member 152 of the tool nest 60 are protuberances or guide pins 160 which are intended to align the package tray thereon for appropriate positioning on the plate member 152, with the tray adapted to be retained thereon through the application of a vacuum to the exterior plate member surface through passageways communicating with a vacuum source connected thereto through the tool nest housing 140.

Figure 7:
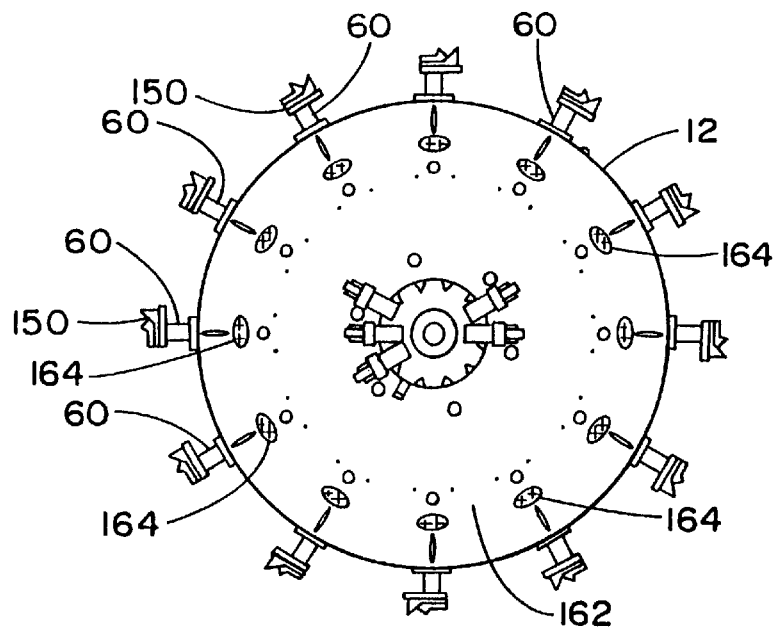
FIG. 7 illustrates a bottom view of the dial or turntable mounting the tool nests, showing vacuum ports for communicating the tool nests and suture capturing and tensioning devices with vacuum-generating source means.
Figure 8:
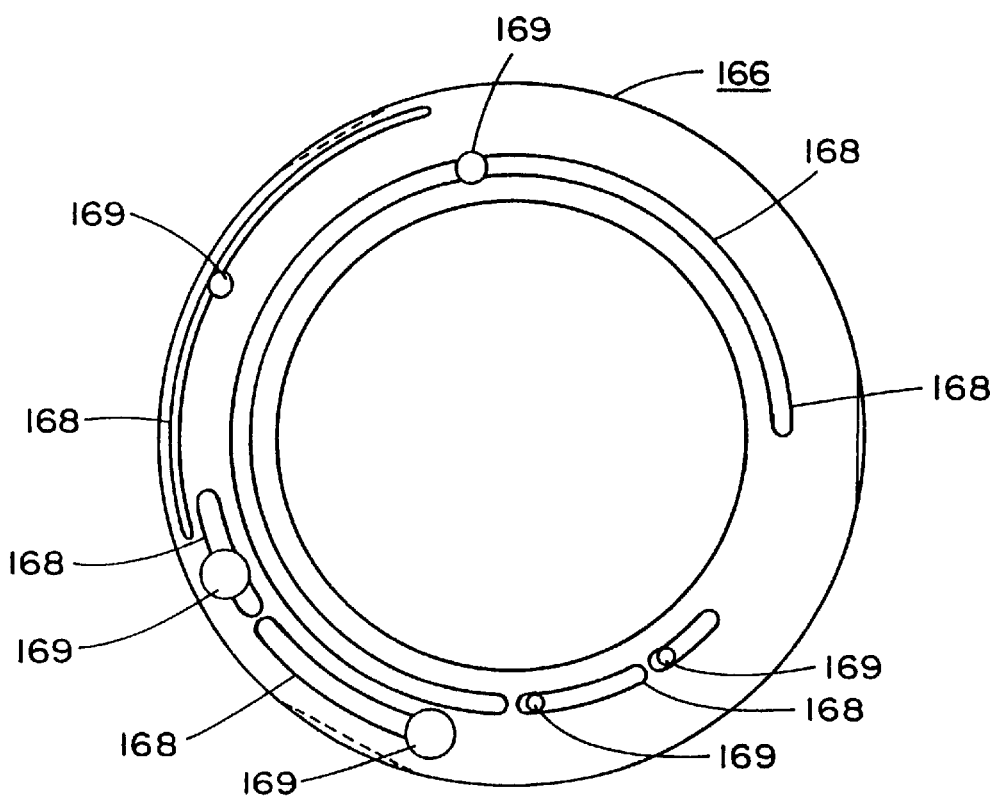
FIG. 8 illustrates a vacuum plenum for supplying the tool nests and devices with controlled vacuum conditions.

The vacuum passageways extend through the lower surface 162 of the dial or turntable 12, as shown in FIG. 7, which includes a plurality of apertures 164 each communicating with, respectively, passageways leading to an associated tool nest 60. The vacuum is supplied to the apertures 164 in a selective controlled mode through the intermediary of a stationary vacuum plenum 166 arranged below the dial 12, as shown in FIG. 2 of the drawings. The plenum 166, as shown in FIG. 8, includes outlet slots 168 and ports 169 for applying or closing a vacuum to respective tool nests 60 in accordance with the rotational positions of the dial 12 with the aperture or ports 164 in the lower surface 162 being in communication with the vacuum plenum outlet slots or ports.

Figure 9:
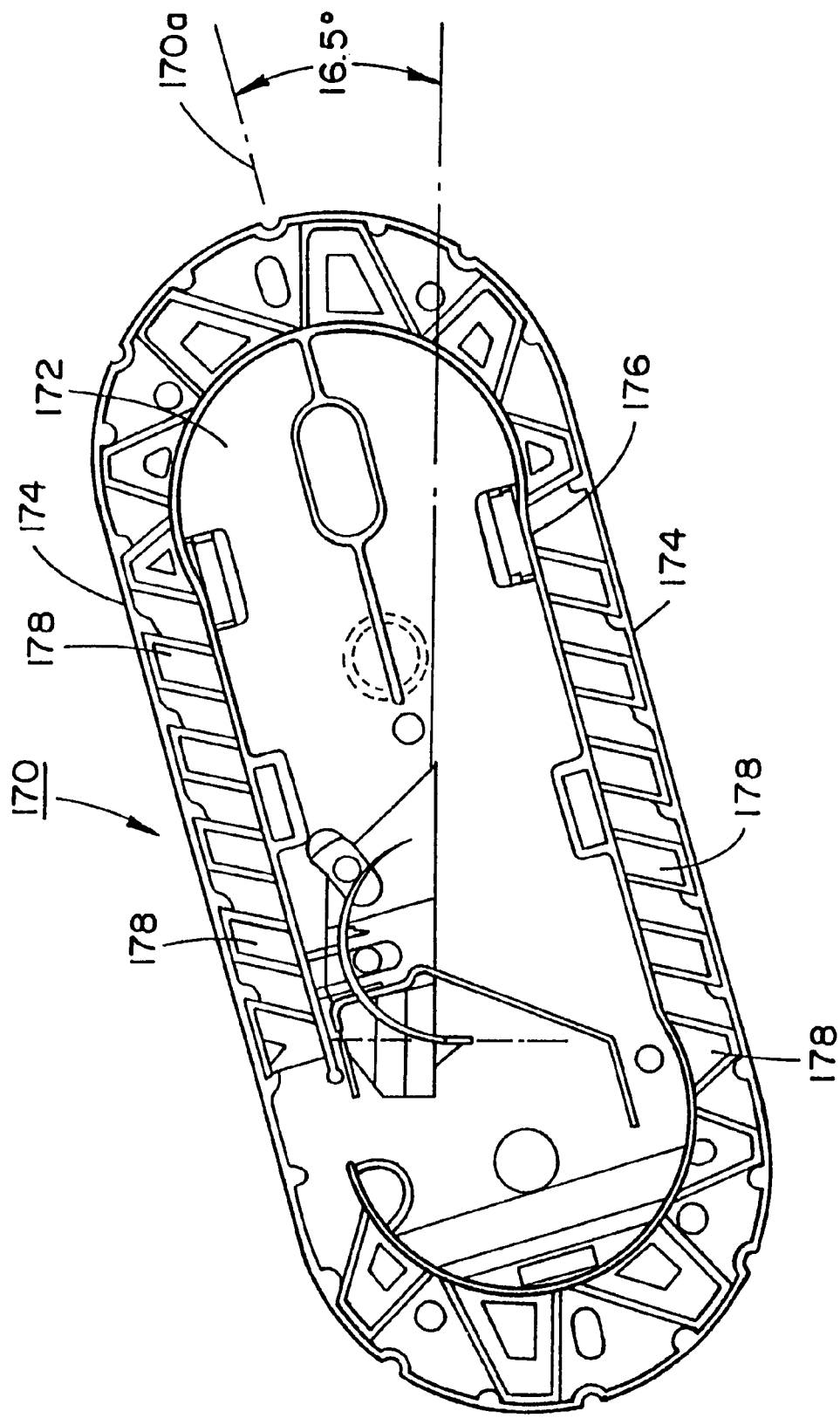
FIG. 9 illustrates a packaging tray with an inserted surgical needle and attached suture, with a portion of the suture extending outwardly and downwardly of the tray.
Figure 10:
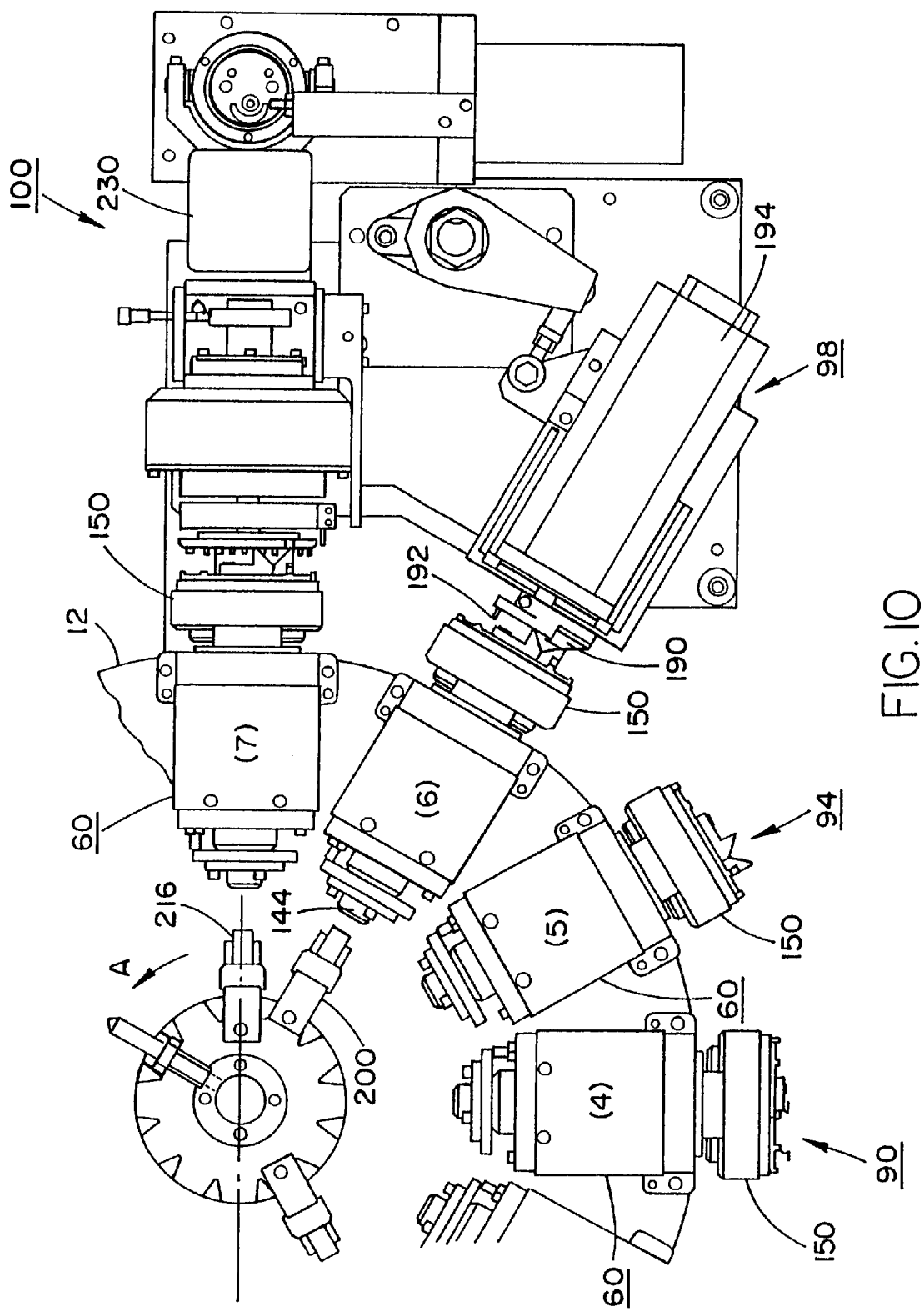
FIG. 10 illustrates a top plan view of the suture winding stations of the packaging machine.
Figure 14:
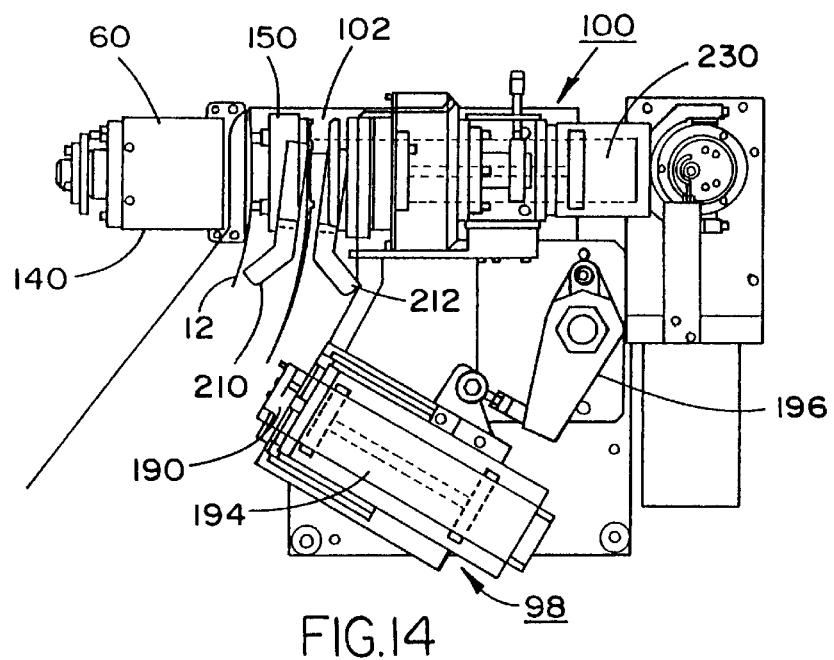
FIG. 14 illustrates a top plan view of the winding stations.

The suture package tray 170, as shown in FIG. 9 of the drawings, is essentially constituted of molded plastic material, and includes a planar base 172 with parallel sides and semi-circular rounded ends. A vertical wall 174 extends about the perimeter of the tray, while inwardly spaced thereof is a second vertical wall 176 having radially outwardly extending fingers 178 which are flexible at the upper edge reaching close to the outer wall 174 so as to define a hollow channel structure. Apertures and surgical needle engaging structure is molded into the tray, as more specifically disclosed in copending U.S. Pat. No. 5,660,024, the disclosure of which is incorporated herein by reference, and which is commonly assigned to the assignee of this application.

At the first winding workstation 98 (6) in the direction of rotation of the turntable 12 along arrow A downstream of the needle transfer workstation 90 (4) where a surgical needle and attached suture were introduced into the package tray 170 by a suitable transfer mechanism, winding apparatus operating structure 96 as detailed hereinbelow, imparts a pivoting displacement to the packaging tray 170. Concurrently, a vacuum-operated clamping unit 180 capturing the suture and vacuum nozzle 182 for tensioning the portion or length of the suture depending outwardly of tray 170 maintain their function, as described in copending application Ser. No. 09/019,674, the disclosure of which is incorporated herein by reference. In this connection, the vacuum-operated unit engages the suture until the latter is to be fully wound into the package tray 170 while concurrently the plurality of vacuum nozzles imparts tension to the suture so as to prevent the suture from snagging during the process of being wound into the package tray 170 at the second winding station 100 (7).

Figure 12:
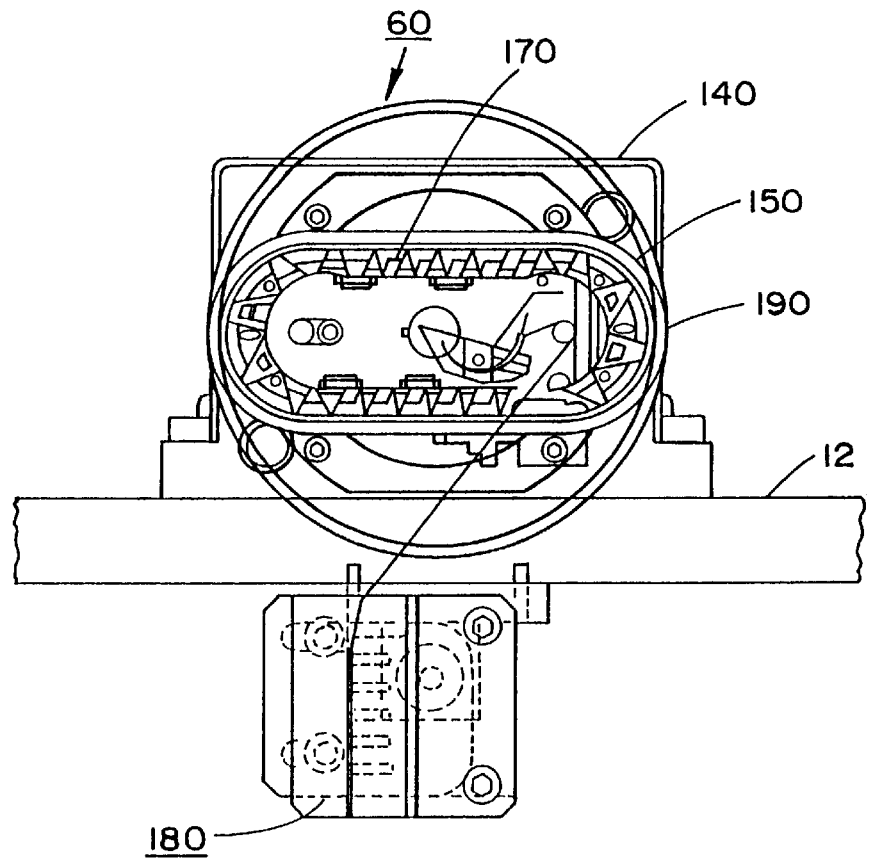
FIG. 12 and 13 illustrate, respectively, front and side views of a tool nest mounting a packaging tray and suture vacuum capture and clamping unit.

At the first winding workstation 98 (6), a winder head 190 of the winding apparatus 96 includes pin structure 192 which upon advance of slide bracket 194 towards the tool nest 60, engages the support plate 150 on the tool nest 60 on which the packaging tray 170 is mounted, this advance being caused by a pivot arm element 196, and drive means (not shown) imparts rotation thereto counterclockwise through an angle of approximately 163.5°. This, in effect, inverts the longitudinal orientation of the package tray 170 about is axis 170a and of the needle contained therein, while orienting the longitudinal tray axis horizontally as shown in FIG. 12, it previously having been imparted an angular counterclockwise tilt of about 16.5° to facilitate the insertion into the tray 170 of the surgical needle and attached suture at the needle transfer workstation 90 (4). The apparatus for effecting the foregoing initial winding includes the rotatable winder head 190 which intermittently advances by means of slide bracket 194 which is activated by pivot arm element 196 towards and through pin 192 into engagement with the tool nest 60 so as to be able to impart rotation to the tray 170, and then retracts after having rotated the tool nest plate member 150 and the package tray 170 mounted thereon through the above-mentioned angle of 163.5°. In this connection, the shaft 144 in the tool nest 60 has been released from engagement to the tool nest housing 140 so as facilitate rotation thereof and axial movement into contact with a cam 200 mounted on turntable 12. This allows the plate member 150 to rotate with the winder head 190, and upon completion of rotation, the slide bracket 194 holding the winding head 190 is retracted in housing 140 of the tool nest 60 so as to cause the shaft 144 to retract, and pins in the housing secures the plate member 150 in its rotated position.

Figure 13:
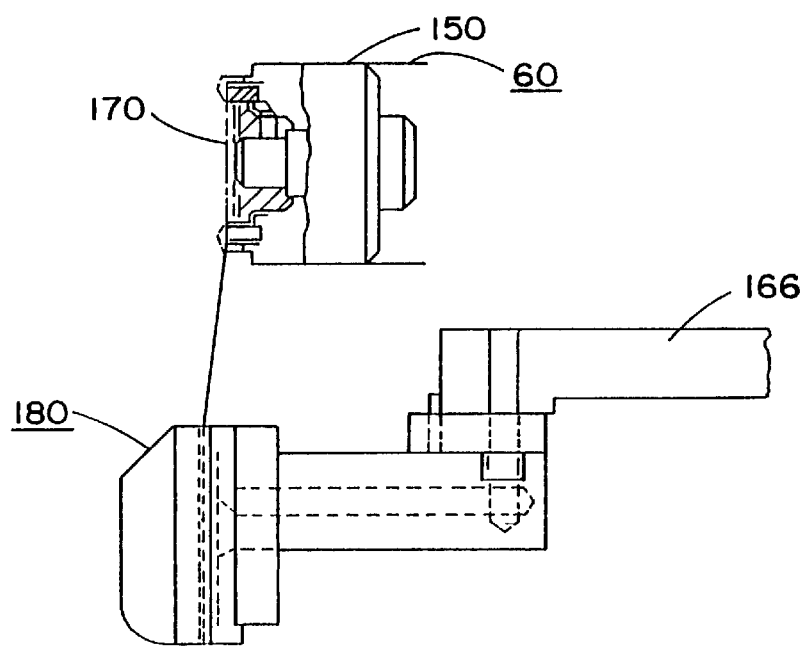
Figure 15:
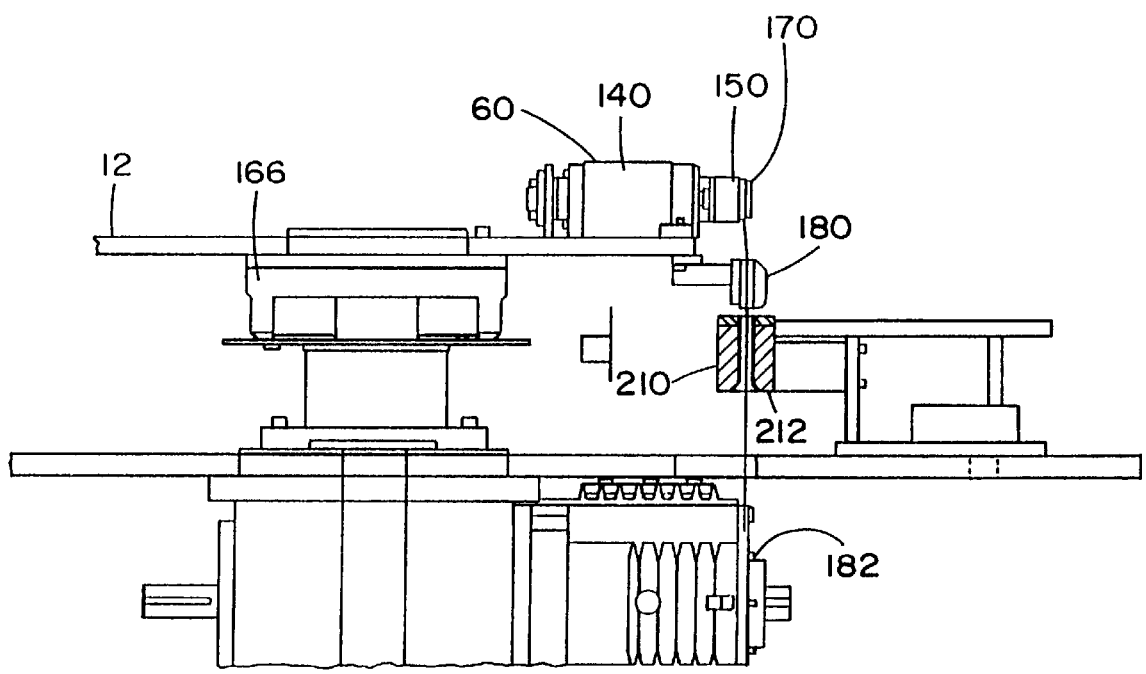
FIG. 15 illustrates a side view of the vacuum tensioning arrangements for the suture.

The invertedly oriented package tray 170, as shown in FIGS. 12 and 13, is advanced by turntable 12 to the second winding station (7), with a portion of the suture still depending downwardly and being engaged by the vacuum clamping unit 180 and tensioned by the vacuum nozzles or fingers 182, and is guided between vacuum guide plate elements 210, 212 below the clamping unit 180. The shaft 144 in tool nest housing 140 is released, as in the instance of the first winding workstation, and extended to contact cam 216 on dial 12, as described above, to allow plate 150 to rotate with the tray 170. Lifting surfaces 218 on winder head 220, the latter of which, as shown in FIGS. 16 to 19, has a shape with longitudinal straight sides 222, 224 and convex ends 226, 228, and which is mounted on winder 102, is adapted to cooperatively engage finger structure extending over the peripheral channel in the tray 170. Accordingly, during rotation of the plate member 150 and tray 170 on the tool 60, the raised fingers of the tray 170 will allow for guiding the suture into the peripheral tray channel. A so-called "zipper" winding mechanism of this type is described in U.S. Pat. No. 5,660,024, the disclosure of which is incorporated herein by reference. This winding rotation of the winder 102 is imparted by means of a drive 230 which rotates the package tray 170 at a high rate of speed over a plurality of rotations commensurate with the length of the particular suture portion extending therefrom, so as to cause the entire length of suture to be wound in one or more circumferential windings into the peripheral channel formed in the package tray 170.

Figure 11:
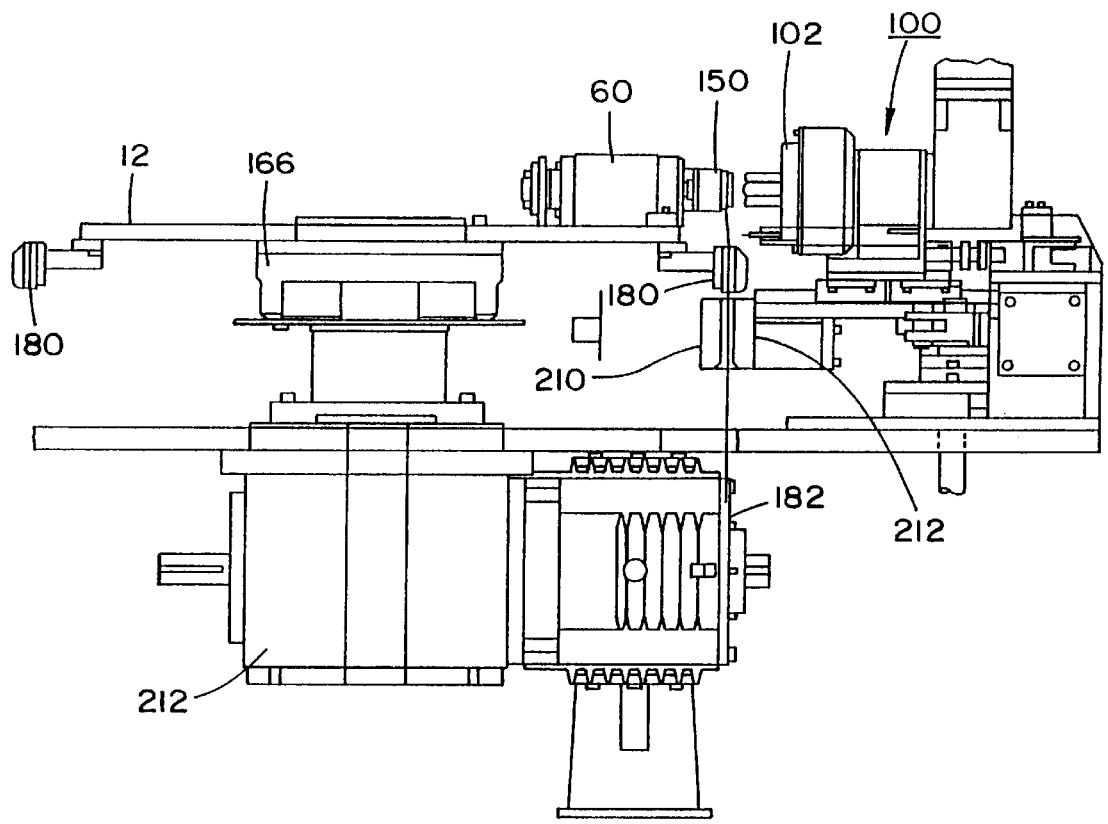
FIG. 11 illustrates a generally diagrammatic side view of the winding stations of FIG. 10.
Figure 11A:
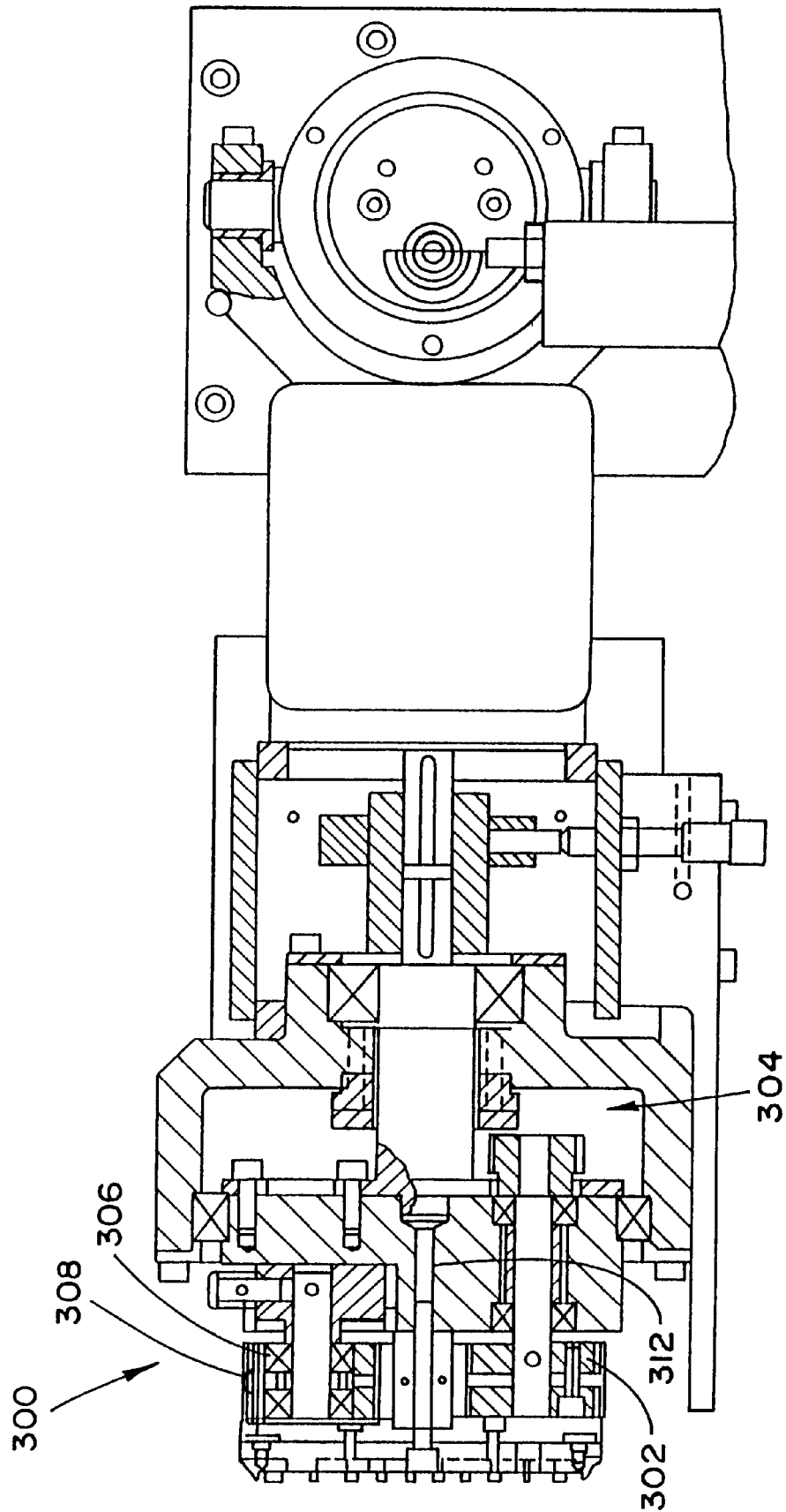
FIG. 11a illustrates a partial sectional view of the suture winding arrangement showing the planetary gearing system.
Figure 11B:
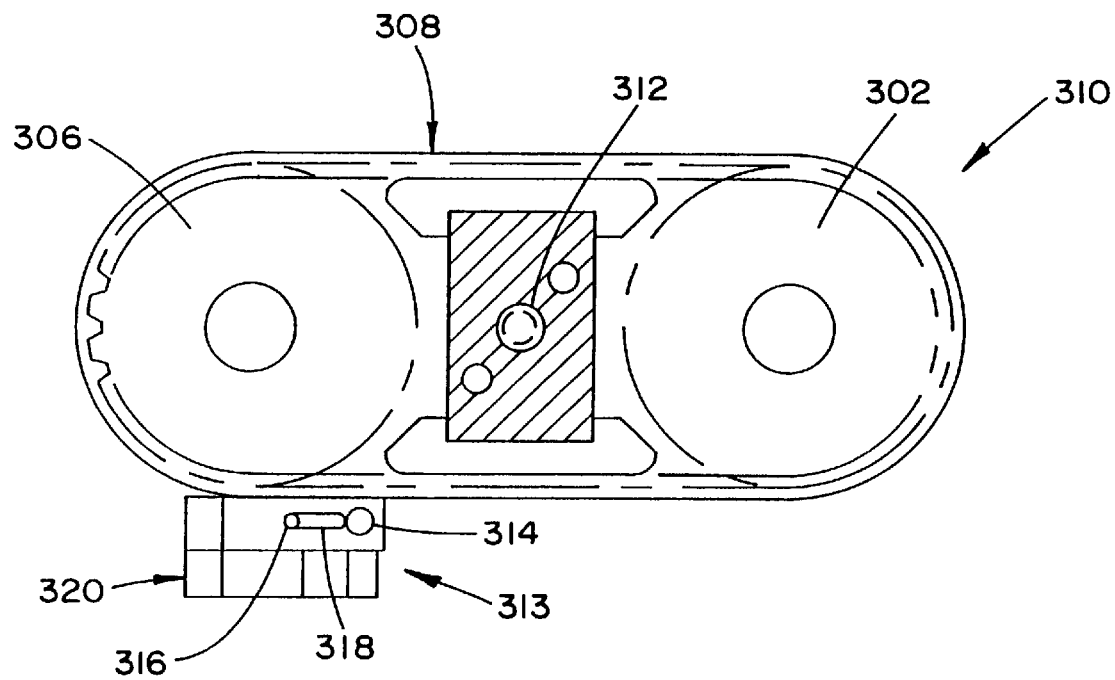
FIG. 11b and 11c illustrate front and top views, respectively, of the planetary gear subassembly.
Figure 11C:
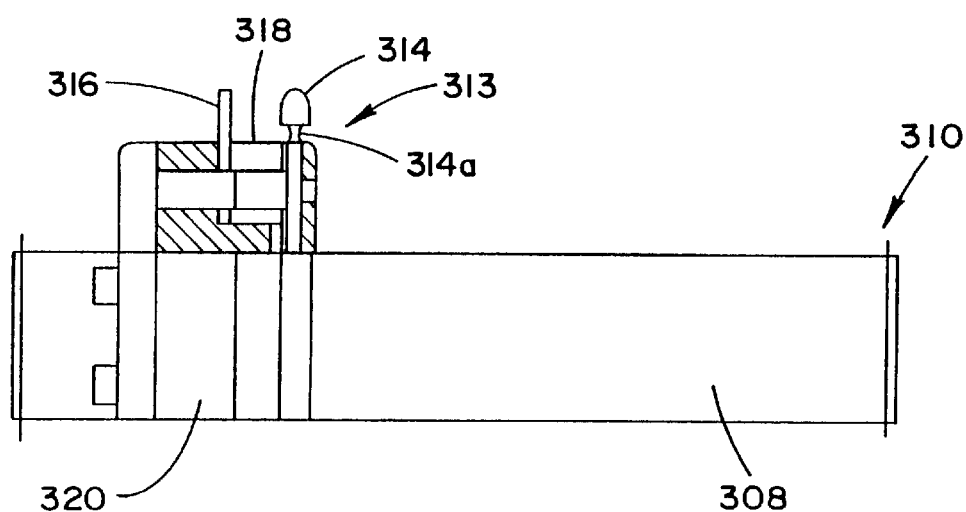

To maintain the suture's position while the winding head 220 is being rotated, a counter-rotating planetary gear system 300 is employed. Referring to FIGS. 11*a* through 11*c*, the planetary gear system 300 is shown in greater detail. The planetary gear system 300 comprises a driven gear 302 which is driven in an opposite direction to the winding head 220 through the winding head motor by a suitable gearing system 304. The driven gear 302 in turn drives idler gear 306 by way of pulley 308 meshably connected thereto. The driven gear 302, idler gear 306, and pulley form a sub-assembly 310 shown in FIGS. 11*b* and 11*c*, which freely rotates about a central shaft 312. Thus, the planetary gear sub-assembly 310 rotates in an opposite direction to the winding head 220 about the same central axis. Attached to the pulley 308 by a suitable bracket 320 is a suture guide assembly 313 comprising a fixed pin 314 having a notch 314*a* for location of the suture, and a movable pin 316 which moves in a slot 318. The movable pin 316 moves into engagement with the stationary pin 314 to clamp the suture therebetween by the application of air pressure acting on a piston (not shown) connected thereto. Application of a vacuum to the same piston retracts the movable pin 316.

Before winding the suture, the suture is clamped by both the clamping unit 180 and the suture guide assembly 313 which defines the sutures path during winding. This defined path is maintained during rotation of the winding head 220 because the planetary gear system 300 maintains the suture guide assembly 313 at a fixed point by way of its counter rotation with respect to the winding head 220.

Thereafter, the winder head 220 is retracted from the tool nest 60, the shaft 144 is released from contact with the cam 216 by the slide bracket 194, and the movable pin 316 of the suture guide assembly 313 is retracted, resultingly locking the plate element 150 in predetermined horizontally extending position. Intermediate the rapid winding workstation 100 (7) and a subsequent cover-applying workstation (9), there may optionally be arranged workstation 106 (8) comprising a sensor 104 which is adapted to ascertain the presence of the surgical needle in the package tray 170.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A suture winding arrangement in a machine for the automated packaging of a single needle having an attached suture to produce a suture package, wherein said machine includes automatically winding said suture within the confines of a tray and attaching a cover to said tray so as to constitute said suture package, said machine having at least one tool nest for supporting said tray, and means for imparting a forwarding motion to said tool nest and said tray supported thereon for indexed advance to a plurality of workstations stationarily arranged proximate the path of advancing movement of said at least one tool nest; said suture winding arrangement comprising:

(a) a first workstation including means for imparting a predetermined rotational movement to the tray which has a surgical needle retained therein with an attached suture having a portion extending outwardly and downwardly from said tray, wherein said at least one tool nest includes locking pin means for locking said means for imparting the predetermined rotational movement to said tray in a first predetermined rotational position and releasing said means for subsequent rapid rotational movement; and (b) a second workstation including means for imparting said rapid rotational movement to said previously rotated tray so as to completely wind said depending suture portion into the confines of said tray.

2. An arrangement as claimed in claim 1, wherein rotation-imparting means at said first workstation rotates said tray to said predetermined rotational position which is 180° inverted relative to the initial orientation of said tray on said at least one tool nest.

3. An arrangement as claimed in claim 2, wherein said rotation-imparting means comprises a winder head reciprocable towards and away from said tray on a support surface of said at least one tool nest, said winder head being engageable with said support surface in the forwardly extended position of the winder head; and drive means for imparting rotation to said winder head for rotating said tray.

4. An arrangement as claimed in claim 3, wherein the support surface on said at least one tool nest is fastened to a rotatable shaft extending through said at least one tool nest; wherein said locking pin means secures said shaft against relative rotation, said locking pin means releasing said shaft for axial movement and rotation to facilitate said winder head imparting the rotational movement to said tray and support surface.

5. An arrangement as claimed in claim 4, wherein a cam structure is contacted by an opposite end of said shaft to limit the axial movement of said shaft.

6. An arrangement as claimed in claim 4, wherein said shaft releasing means comprises a slide bracket mechanism.

7. An arrangement as claimed in claim 1, wherein said rapid rotation imparting means at said second workstation comprises a winder head structure engageable with said tray and a support surface on said at least one tool nest for winding the extending portion of the suture into said tray.

8. An arrangement as claimed in claim 7, wherein said winder head structure at said second workstation comprises protruding means which are engageable with surface structure on said tray so as to facilitate winding of said depending suture portion into a peripheral channel formed in said tray.

9. An arrangement as claimed in claim 7, wherein said winder head structure at said second winding workstation is rotated at a high rotational speed.

10. An arrangement as claimed in claim 7, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

11. An arrangement as claimed in claim 10, wherein a cam structure is contacted by an opposite end of said shaft to limit the axial movement of said shaft.

12. An arrangement as claimed in claim 11, wherein said locking pin means locks said shaft in a second predetermined rotational position upon completing the winding of the suture into said tray.

13. An arrangement as claimed in claim 10, wherein said shaft releasing means comprises a slide bracket mechanism.

14. A method of winding sutures in a machine for the automated packaging of a single needle having an attached suture to produce a suture package, wherein said machine includes automatically winding said suture within the confines of a tray and attaching a cover to said tray so as to constitute said suture package, said machine receiving said single needle having an attached suture in a vertical plane orientation from a gripper means and further having at least one tool nest for supporting said tray, and imparting a forwarding motion to said tool nest and said tray supported thereon for indexed advance to a plurality of workstations stationarily arranged proximate the path of advancing movement of said at least one tool nest; said suture winding method comprising:

(a) at a first workstation imparting a predetermined rotational movement in the vertical plane to the tray which has a surgical needle retained therein with an attached suture having a portion extending outwardly and downwardly from said tray; and (b) at a second workstation imparting rapid high speed rotational movement in the vertical plane to said previously rotated tray so as to completely wind said depending suture portion into the confines of said tray.

15. A method as claimed in claim 14, wherein at said first workstation the imparting step comprises rotating said tray to assume an orientation which is 180° inverted relative to the initial orientation of said tray on said at least one tool nest.

16. A method as claimed in claim 15, wherein said rotating comprises the steps of: reciprocably moving a winder head towards and away from said tray on a support surface of said at least one tool nest, said winder head being engageable with said support surface in the forwardly extended position of said winder head; and imparting rotation to said winder head for rotating said tray when said winder head is in the forwardly extendable position.

17. A method as claimed in claim 16, wherein the support surface on said at least one tool nest is fastened to a rotatable shaft extending through said at least one tool nest; said shaft being normally secured against relative rotation, further comprising the step of releasing said shaft for axial movement and rotation to facilitate said winder head imparting the rotational movement to said tray and support surface.

18. A method as claimed in claim 17, further comprising the step of contacting a cam structure by an opposite end of said shaft to limit the axial movement of said shaft.

19. A method as claimed in claim 18, further comprising the step of locking said shaft in a predetermined rotational position with a locking pin means included on said at least one tool nest, said locking pin means being responsive to deactivation of release means so as to maintain said tray in said rotationally inverted position on said support surface.

20. A method as claimed in claim 14, further comprising the step of engaging said tray with a winder head structure and a support surface on said at least one tool nest for imparting said rapid high speed rotation at said second workstation for winding the extending portion of the suture into said tray.

21. A method as claimed in claim 20, wherein the support surface on said at least one tool nest is fastened to a rotatable shaft extending through said at least one tool nest; normally securing said shaft against relative rotation, further comprising the step of releasing said shaft for axial movement and rotation to facilitate said winder head imparting the rotational movement to said tray and support surface.

22. A method as claimed in claim 21, further comprising the step of contacting a cam structure by an opposite end of said shaft to limit the axial movement of said shaft.

23. A method as claimed in claim 22, further comprising the step of locking said shaft in a predetermined rotational position with a locking pin means included on said at least one tool nest, said locking pin means being responsive to deactivation of release means so as to maintain said tray in said rotationally inverted position on said surface upon completion of winding of the suture.

24. A method as claimed in claim 14, further comprising the step of imparting tension to the depending suture portion prior to and during the winding of the suture into said tray.

25. A suture winding arrangement in a machine for the automated packaging of a single needle having an attached suture to produce a suture package, wherein said machine includes automatically winding said suture within the confines of a tray and attaching a cover to said tray so as to constitute said suture package, said machine receiving said single needle having an attached suture in a vertical plane orientation from a gripper means and further having at least one tool nest for supporting said tray, and means for imparting a forwarding motion to said tool nest and said tray supported thereon for indexed advance to a plurality of workstations stationarily arranged proximate the path of advancing movement of said at least one tool nest; said suture winding arrangement comprising:

(a) a first workstation including means for imparting a predetermined rotational movement in the vertical plane to the tray which has a surgical needle retained therein with an attached suture having a portion extending outwardly and downwardly from said tray; and (b) a second workstation including means for imparting rapid high speed rotational movement in the vertical plane to said previously rotated tray so as to completely wind said depending suture portion into the confines of said tray.

26. An arrangement as claimed in claim 25, wherein rotation-imparting means at said first workstation rotates said tray so as to assume an orientation which is 180° inverted relative to the initial orientation of said tray on said at least one tool nest.

27. An arrangement as claimed in claim 26, wherein said rotation-imparting means comprises a winder head reciprocable towards and away from said tray on a support surface of said at least one tool nest, said winder head being engageable with said support surface in the forwardly extended position of the winder head; and drive means for imparting rotation to said winder head for rotating said tray.

28. An arrangement as claimed in claim 27, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

29. An arrangement as claimed in claim 25, wherein said rapid rotation imparting means at said second workstation comprises a winder head structure engageable with said tray and a support surface on said at least one tool nest for winding the extending portion of the suture into said tray.

30. An arrangement as claimed in claim 29, wherein said winder head structure at said second workstation comprises protruding means which are engageable with surface structure on said tray so as to facilitate winding of said depending suture portion into a peripheral channel formed in said tray.

31. An arrangement as claimed in claim 29, wherein said winder head structure at said second winding workstation is rotated at a high rotational speed.

32. An arrangement as claimed in claim 29, wherein the support surface on said at least one tool nest is fastened to a rotatable shaft extending through said at least one tool nest; means normally securing said shaft against relative rotation, said means releasing said shaft for axial movement and rotation to facilitate said winder head imparting the rotational movement to said tray and support surface.

33. An arrangement as claimed in claim 25, wherein suture tensioning means impart tension to the depending suture portion prior to and during the winding of the suture into said tray.

34. An arrangement as claimed in claim 33, wherein said suture tensioning means comprises a plurality of vacuum nozzles.

35. An arrangement as claimed in claim 33, wherein further vacuum tensioning means impart tension to a trailing end of said depending suture portion until said suture is completely wound into said tray.

36. An arrangement as claimed in claim 25, wherein a plurality of said tool nests are mounted on a turntable, said workstations being spaced about the periphery of said turntable.

37. A suture winding arrangement in a machine for the automated packaging of a single needle having an attached suture to produce a suture package, wherein said machine includes automatically winding said suture within the confines of a tray and attaching a cover to said tray so as to constitute said suture package, said machine having at least one tool nest for supporting said tray, and means for imparting a forwarding motion to said tool nest and said tray supported thereon for indexed advance to a plurality of workstations stationarily arranged proximate the path of advancing movement of said at least one tool nest; said suture winding arrangement comprising:

(a) a first workstation including means for imparting a predetermined rotational movement to the tray which has a surgical needle retained therein with an attached suture having a portion extending outwardly and downwardly from said tray; and (b) a second workstation including means for imparting rapid rotational movement to said previously rotated tray so as to completely wind said depending suture portion into the confines of said tray, the second workstation further including means for maintaining an end of the depending suture portion stationary while the suture is wound into the confines of said tray.

38. An arrangement as claimed in claim 37, wherein the means for maintaining the suture stationary comprises a counter-rotating means for counter-rotating relative to the predetermined rotational movement and a suture guide assembly attached to the counter-rotating means for clamping the end of the depending suture portion in the stationary position, wherein due to the counter-rotation of the suture guide assembly there is no relative movement between it and the depending suture portion.

39. An arrangement as claimed in claim 38, wherein the counter-rotating means comprises a planetary gear system having a driven gear driven opposite the direction of the predetermined rotational movement and an idler gear meshably connected to the driven gear by way of a pulley belt, wherein the pulley belt rotates in a direction opposite the direction of the predetermined rotational movement about a central axis also about which the tray rotates.

40. An arrangement as claimed in claim 35, wherein the suture guide assembly is fixed to the pulley belt and comprises a fixed pin and a slidable pin, the end of the suture depending portion being clamped between said fixed and slidable pins when the slidable pin is moved from a release position to a clamped position.

* * * * *